United States Patent [19]
Iwamoto et al.

[11] Patent Number: 4,920,804
[45] Date of Patent: May 1, 1990

[54] INSERT TYPE ULTRASONIC CRACK HUNTING APPARATUS

[75] Inventors: Keiichi Iwamoto; Masaaki Torichigai, both of Nagasaki, Japan

[73] Assignee: Mitsubishi Jukogyo Kabushiki Kaisha, Tokyo, Japan

[21] Appl. No.: 260,514

[22] Filed: Oct. 20, 1988

[30] Foreign Application Priority Data

Oct. 27, 1987 [JP] Japan .................. 62-269452

[51] Int. Cl.$^5$ .............................................. G01N 29/04
[52] U.S. Cl. ...................................................... 73/623
[58] Field of Search ............. 73/622, 623, 621, 40.5 A

[56] References Cited

U.S. PATENT DOCUMENTS

| | | | |
|---|---|---|---|
| 3,845,463 | 10/1974 | Timbs ................................. | 73/623 |
| 4,096,757 | 6/1978 | Ishii et al. ........................... | 73/623 |
| 4,160,385 | 7/1979 | Gromlich et al. ................... | 73/622 |
| 4,663,727 | 5/1987 | Saporito et al. .................... | 73/623 |

Primary Examiner—Hezron E. Williams
Assistant Examiner—Louis M. Arana
Attorney, Agent, or Firm—Wenderoth, Lind & Ponack

[57] ABSTRACT

An improved insert type supersonic crack hunting apparatus is capable of discovering cracks in a boiler steel tube from inside the tube. A crack hunting section provided with a probe, a slip ring for transmitting an ultrasonic signal issued from the probe, a rotary use motor for rotary the crack hunting section and an axial feed motor for moving the crack hunting section in an axial direction are connected in sequence. An axial feed nut for converting rotation of the axial feed motor into movement in the axial direction is disposed between the rotary use motor and the axial feed motor. In addition, there is provided a coupling section, in which a front end of a flexible shaft connected to the axial feed motor is coupled to a rear end of a shaft connected to the axial feed nut. An axial feed shaft thrust bearing for supporting the coupling section is disposed between the axial feed nut and the axial feed motor. Preferably, a geared shaft at the front end of the shaft having its rear end coupled to the flexible shaft connected to the axial feed motor, is threadedly inserted into the axial feed nut.

6 Claims, 3 Drawing Sheets

INSERT TYPE ULTRASONIC CRACK HUNTING APPARATUS

BACKGROUND OF THE INVENTION

1. Field of the Invention

The present invention relates to an ultrasonic crack discovering apparatus for hunting cracks generated in a tube such as cracks occurring in welded portions of a boiler steel tube, from inside the tube.

2. Prior Art

With regard to boiler steel pipes, since generally a large number of steel tubes are arrayed within a boiler very close to one another, welded portions of boiler steel tubes, where occurrence of cracks are feared, have been almost not accessible for the purpose of crack hunting. Consequently, in the prior art, after the boiler steel tubes in a panel form had been carried to the outside of a boiler by spending a lot of man-hours, the welded portions were ground and magnetic-powder crack hunting was carried out on the ground portions.

As described above, in the prior art, an inspection of welded portions (especially welded portions with spacers) of boiler steel tubes was almost unable to be executed with the boiler in its original state because of a narrow space for access to the welded portions.

Therefore, the boiler steel tubes were cut out for each panel and carried to the outside of a furnace with a crane, and grinding and subsequent magnetic-powder crack hunting were performed outside the furnace. And after finishing the inspection, the panel was carried into the furnace again with a crane, and welding was performed to restore the boiler to its original state. Howver, since the work necessitates enormous man-hours, its cost was high, and hence, the establishment of a simple and convenient alternative method to be employed has been desired.

SUMMARY OF THE PRESENT INVENTION

It is therefore one object of the present invention to provide a novel insert type ultrasonic crack hunting apparatus which overcomes the above-mentioned drawback in the prior art.

According to one feature of the present invention, there is provided an insert type ultrasonic crack hunting apparatus, wherein a crack hunting section provided with a probe, a slip ring for transmitting an ultrasonic signal issued from the probe, a rotary use motor for the crack hunting section, and an axial feed motor for the crack hunting section are connected in sequence, an axial feed nut for converting rotation of the axial feed motor into movement in the axial direction is disposed between the rotary use motor and the axial feed motor, a coupling section is provided in which a front end of a flexible shaft connected to the axial feed motor is coupled to a rear end of a shaft connected to the axial feed nut, and an axial feed shaft thrust bearing for supporting the coupling section is disposed between the axial feed nut and the axial feed motor.

According to another feature of the present invention, there is provided the above-featured insert type ultrasonic crack hunting apparatus, wherein a geared shaft at the front end of the shaft having its rear end coupled to the flexible shaft connected to the axial feed motor, is threadedly inserted into the axis feed nut.

During the operation of the above-described insert type crack hunting apparatus according to the present invention, the crack hunting section of the apparatus is inserted into a tube up to a location where crack hunting is to be carried out, by any appropriate means such as pressurized water or the like. Subsequently, the crack hunting section is rotated within the tube by rotating the rotary use motor; simultaneously the axis feed motor is rotated, and hence, the crack hunting section is moved in the axial direction by the conversion of the rotation of the axial feed motor into axial movement with the aid of the axial feed nut. By simultaneously rotating and moving in the axial direction the crack hunting section in the above-described manner, the probe is moved in a spiral manner, and thereby necessary crack hunting is effected over the entire inner circumferential surface of the tube.

Furthermore, since the axial feed motor is coupled to the members located in front at the axial feed shaft thrust bearing via the flexible shaft, even in the event that an excessively large force is exerted on the front portion of the apparatus, for example, by pressurized water upon inserting the apparatus into a tube, this force will not be directly transmitted to the axial feed motor, and so, damage of the motor caused by such an axial force can be prevented.

The above-mentioned and other objects, features and advantages of the present invention will become more apparent by referring to the following description of the preferred embodiment of the invention taken in conjunction with the accompanying drawings.

DETAILED DESCRIPTION OF THE PREFERRED EMBODIMENT

Figure 1:
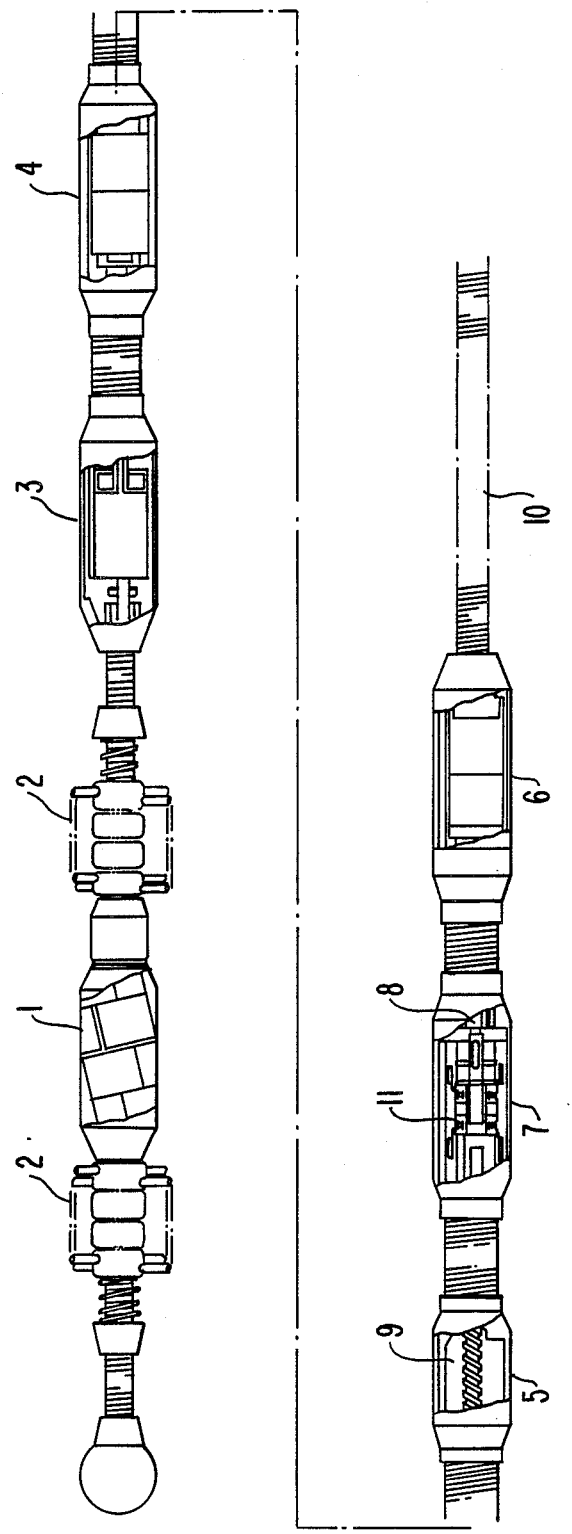
FIG. 1 is a side view, partly cut away, of one preferred embodiment of the present invention.

Now the preferred embodiment of the present invention will be described with reference to FIGS. 1 to 3.

Reference numeral 1 designates a crack hunting section having one or more ultrasonic probes in which the frequency type, and incident angle, etc. of the wave issued are preset so as to enable the detection of object defects during crack hunting at the highest degree of sensitivity, and a pair of centering members 2, 2 for holding the crack hunting section and mounted in front of and behind the same crack hunting section. A slip ring 3 for smoothly transmitting a crack detection signal issued from a rotating probe through cable 10 to a an ultrasonic crack detector, (not shown) operatively connected to cable 10 for analyzing the signal to detect the presence of cracks, a rotary use motor 4 for rotating the crack hunting section 1, an axial feed nut 5 for moving the above-mentioned crack hunting section 1, slip ring 3 and rotary use motor 4 in the axial direction, and an axial feed motor 6 for moving the crack hunting section 1 in the axial direction, are sequentially disposed on the rear side (on the right side as viewed in FIG. 1) of the above-described crack hunting section. The above-mentioned respective portions are successively connected with one another via flexible coupling members which can transmit rotation and movement in the axial direction.

Into a female screw portion of the abovedescribed axial feed nut 5, is threadedly inserted a threaded front end portion of a flexible geared coupling shaft 9 from the rear. Reference numeral 7 designates an axial feed shaft thrust bearing provided between the axial feed nut 5 and the axial feed motor 6, in which as shown in FIG. 3, a coupling portion 9' at the rear end of the coupling shaft 9 is supported by a ball bearing 11. The coupling portion 9' is provided with a female screw portion 9'a tapped from the rear, and a threaded portion 8a provided at the front end of a flexible output shaft 8 mounted to the axial feed motor 6 is threadedly inserted into this female screw portion 9'a from the rear.

Reference numeral 10 designates a cable for transmitting an ultrasonic signal to an ultrasonic crack detector (not shown).

Figure 2:
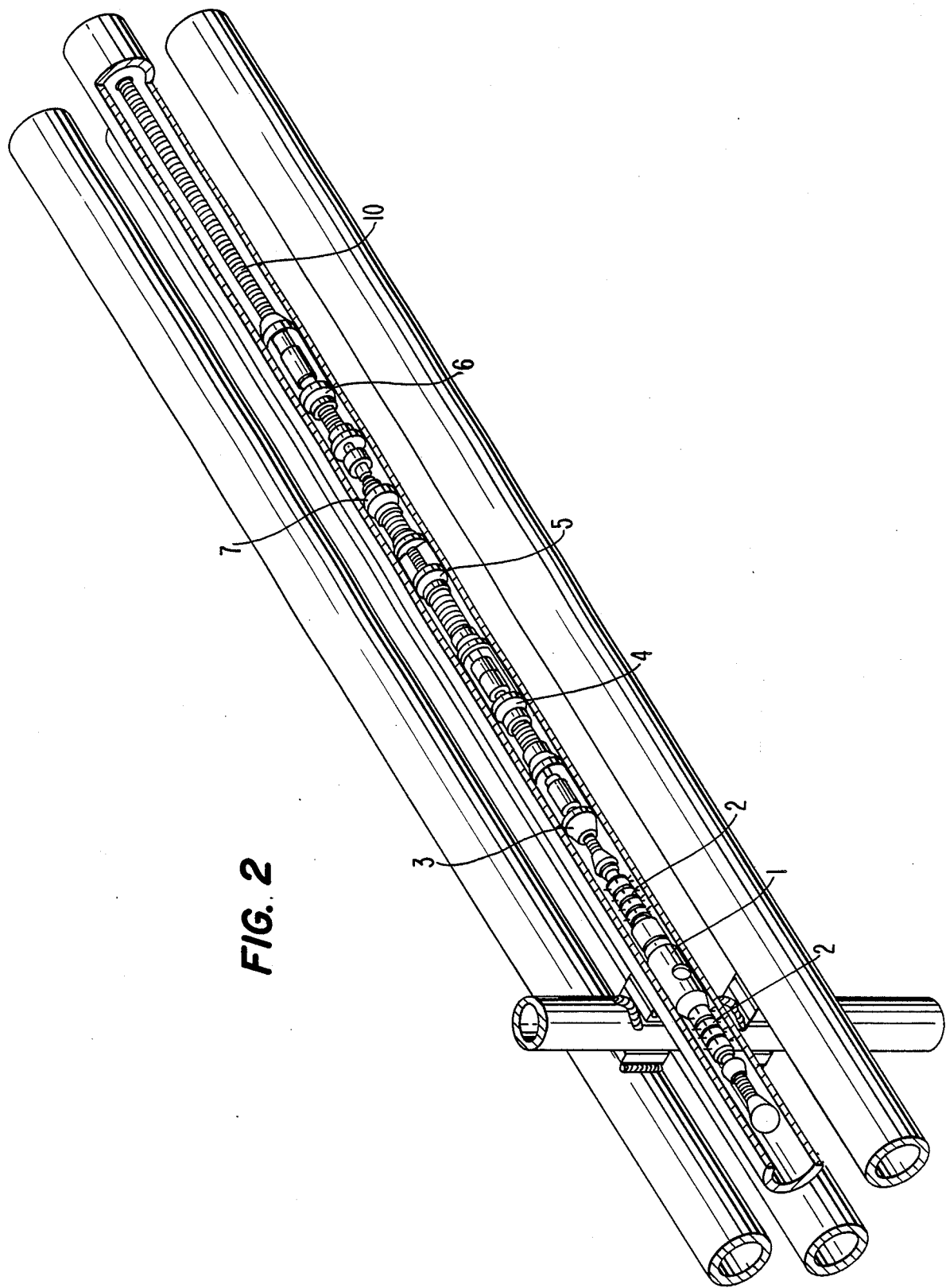
FIG. 2 is a perspective view of the same preferred embodiment as used in crack hunting in a portion of a tube welded to a spacer.

To perform crack hunting with the illustrated embodiment, as shown in FIG. 2, the crack hunting section 1 is carried, for instance, into a boiler steel tube up to a portion welded to a side spacer by means of pressurized water or by any other appropriate means. Subsequently, after it has been confirmed that the axial feed nut 5 has arrived at a limit position on the side of the crack hunting section 1, the rotary use motor 4 and the axial feed motor 6 are energized.

The crack hunting section 1 commences rotation over 360 degrees, accompanying the rotation of the rotary use motor 4. The rotation of the axial feed motor 6 causes the flexible geared coupling shaft 9 to rotate via the flexible output shaft 8 and the axial feed shaft thrust bearing 7. As a result of this rotation of the flexible geared coupling shaft 9, the axial feed nut 5 is drawn towards the axial feed motor 6. Since this axial feed nut 5 is connected with the rotary use motor 4, the slip ring 3 and the crack hunting section 1, these members are jointly drawn towards the axial feed motor 6.

Since the rotation and the movement in the axial direction of the crack hunting section 1 are effected simultaneously in the above-described manner, crack hunting over the above-described welded portion can be carried out in a helical manner. The ultrasonic probes of the crack hunting section 1 may operate in a conventional manner by issuing the aforementioned ultrasonic waves (via transducers, for example), receiving the ultrasonic energy reflected from the welded portion, converting the received energy into signals (via transducers, for example), and transmitting the signals to a conventional ultrasonic crack (flaw) detector via cable 10.

Figure 3:
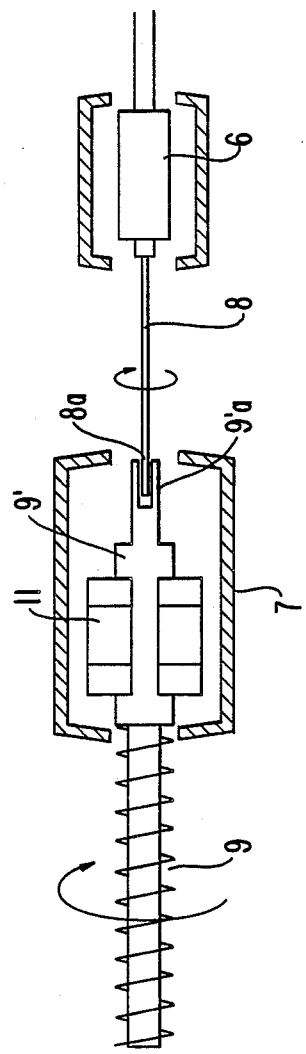
FIG. 3 is a schematic view showing the structure of an axial feed shaft thrust bearing in the same preferred embodiment.

At this time, in the axial feed shaft thrust bearing 7, simultaneously with rotation of the axial feed motor 6, the flexible output shaft 8 also rotates, for example, in the direction shown by an arrow in FIG. 3, and this rotation is transmitted via the above-mentioned screw thread portions 8a, 9'a to the flexible coupling shaft 9 in the above-described manner.

In addition, when an excessively large tensional force in the axial direction is applied to the crack hunting section 1, such as in the case where the crack hunting section 1 is carried into a tube by means of pressurized water, this force is not directly transmitted to the axial feed motor 6 because the flexible output shaft 8 is disposed between the axial feed shaft thrust bearing 7 and the axial feed motor 6, and thus damage of the same motor 6 can be prevented.

As described in detail above, according to the present invention, it is possible to perform crack hunting while the crack hunting section is being moved precisely and smoothly in a spiral manner, and thus to execute reliable crack hunting.

In addition, the drawing out of boiler steel tubes in panel form to the outside of a furnace is not necessity, it is possible to perform an inspection of welded portions with the tubes kept in place, and thus, the expense of inspection for the welded portions can be greatly reduced.

Still further, according to the present invention, even if an excessively large force is applied in the axial direction, this force is prevented from being directly transmitted to the axial feed motor, and so, the axial feed motor can be prevented from being damaged.

While the present invention has been described above in connection with one preferred embodiment, it is a matter of course that many apparently widely different embodiments of the present invention can be made without departing from the spirit of the present invention.

What is claimed is:

1. An insert type ultrasonic crack hunting apparatus comprising:
    a crack hunting section having a rotatable and axially displaceable probe for emitting ultrasound and for issuing signals indicative of the ultrasound that has reflected from a member in which the probe is disposed when emitting the ultrasound;
    a slip ring section including a slip ring operatively connected to said probe for transmitting said signals irrespective of the relative rotational position of said probe;
    a rotary use motor section including a rotary use motor connected to said probe for rotating said probe in the apparatus;
    an axial feed motor section including an axial feed motor for facilitating axial displacement of said probe in the apparatus;
    coupling members connecting said crack hunting section, said slip ring section, said rotary use motor section and said axial feed motor section in an axial serial relationship in the foregoing sequence in the apparatus;
    a feed nut section connected in the apparatus between said rotary use motor and said axial feed motor, said feed nut section including an axial feed nut connected to said axial feed motor for converting a rotational output of said axial feed motor into axial movement to axially displace said rotary use motor section, said slip ring section and said crack hunting section in said apparatus;
    an output shaft connected at one end thereof to said axial feed motor;
    a coupling shaft operatively engaged at one end thereof with said axial feed nut;
    a coupling portion disposed in said apparatus between said axial feed nut and said axial feed motor and coupling said output shaft to said coupling shaft at the other ends of said shafts, said coupling portion transmitting rotational output of said axial feed motor to said axial feed nut; and
    a thrust bearing supporting said coupling portion.

2. An insert type ultrasonic crack hunting apparatus as claimed in claim 1, wherein said coupling shaft is threadingly engaged at said one end thereof with said axial feed nut.

3. An insert type ultrasonic crack hunting apparatus as claimed in claim 1, wherein said coupling members, said output shaft and said coupling shaft are flexible.

4. An insert type ultrasonic crack hunting apparatus comprising:
- a crack hunting section having a rotatable and axially displaceable probe for emitting ultrasound and for issuing signals indicative of the ultrasound that has reflected from a member in which the probe is disposed when emitting the ultrasound;
- a slip ring section including a slip ring operatively connected to said probe for transmitting said signals irrespective of the relative rotational position of said crack hunting section;
- a rotary use motor section including a rotary use motor connected to said probe for rotating said probe in the apparatus;
- an axial feed motor section including an axial feed motor for facilitating axial displacement of said probe in the apparatus;
- coupling members connecting said crack hunting section, said slip ring section, said rotary use motor section and said axial feed motor section in an axial serial relationship in the foregoing sequence in the apparatus; and
- coupling means connected between said axial feed motor and said rotary use motor in the apparatus for receiving a rotational output of said axial feed motor and converting the rotational output into axial movement to axially displace said rotary use motor section, said slip ring section and said crack hunting section in the apparatus.

5. An insert type ultrasonic crack hunting apparatus as claimed in claim 4, wherein said coupling members, said output shaft and said coupling shaft are flexible.

6. An insert type ultrasonic crack hunting apparatus as claimed in claim 4, wherein a thrust bearing is disposed in the apparatus between said axial feed motor and said rotary use motor, said thrust bearing supporting said coupling means.

* * * * *